United States Patent
Jobst et al.

(10) Patent No.: US 7,691,623 B2
(45) Date of Patent: Apr. 6, 2010

(54) METHOD FOR THE FABRICATION OF A "LAB ON CHIP" FROM PHOTORESIST MATERIAL FOR MEDICAL DIAGNOSTIC APPLICATIONS

(75) Inventors: Gerhard Jobst, Eichstetten (DE); Thomas Gamp, Albstadt (DE)

(73) Assignee: Isabella Moser, Eichstetten (DE)

( * ) Notice: Subject to any disclaimer, the term of this patent is extended or adjusted under 35 U.S.C. 154(b) by 1526 days.

(21) Appl. No.: 10/486,681

(22) PCT Filed: Aug. 5, 2002

(86) PCT No.: PCT/EP02/08724

§ 371 (c)(1),
(2), (4) Date: Aug. 30, 2004

(87) PCT Pub. No.: WO03/016912

PCT Pub. Date: Feb. 27, 2003

(65) Prior Publication Data

US 2005/0003519 A1    Jan. 6, 2005

(30) Foreign Application Priority Data

Aug. 13, 2001 (DE) .................................. 101 39 742

(51) Int. Cl.
C12M 1/34    (2006.01)
(52) U.S. Cl. .............. 435/287.2; 435/283.1; 435/286.5; 436/524; 427/2.11
(58) Field of Classification Search ................ None
See application file for complete search history.

(56) References Cited

U.S. PATENT DOCUMENTS

| | | | |
|---|---|---|---|
| 5,212,050 A | 5/1993 | Mier et al. | |
| 6,633,031 B1 * | 10/2003 | Schultz et al. | 250/288 |
| 6,716,620 B2 * | 4/2004 | Bashir et al. | 435/287.2 |
| 2001/0018183 A1 * | 8/2001 | Bao et al. | 435/6 |
| 2001/0053535 A1 * | 12/2001 | Bashir et al. | 435/34 |

FOREIGN PATENT DOCUMENTS

| | | |
|---|---|---|
| WO | WO 00/32678 | 6/2000 |
| WO | WO 00/33084 | 6/2000 |

OTHER PUBLICATIONS

Nicolau et al., Micron-sized protein patterning on diazonaphthoquinon/novolak thin polymeric films; 1998, Langmuir 14: 1927-1936.*
Moser et al., "Rapid liver enzyme assay with miniaturized liquid handling system comprising thin film biosensor array," *Sensors and Actuators B*, No. 44, (1997), pp. 377-380.
Jobst et al., "Application of Miniaturized Liquid Handling System with Integrated Biosensor Array for Milk Analysis," *The 8th International Conference on Solid State Sensors and Actuators, and Eurosensors IX*, (Jun. 1995), pp. 473,474.

* cited by examiner

*Primary Examiner*—N. C. Yang
(74) *Attorney, Agent, or Firm*—Sughrue Mion, PLLC

(57) ABSTRACT

The present invention relates to a device for performing immuno assays ("biochip" or "lab on chip" respectively), a procedure for its fabrication and the use of the device for performing immuno assays. Furthermore the present invention relates to the use of a photo lithographically patternable dry film photo resist based on a material with functional chemical groups for the immobilization of biomolecules.

15 Claims, 2 Drawing Sheets

Processing of a film based on a negative dry film photo resist

Lamination    UV-Exposure    Development

METHOD FOR THE FABRICATION OF A "LAB ON CHIP" FROM PHOTORESIST MATERIAL FOR MEDICAL DIAGNOSTIC APPLICATIONS

This application is the national stage of PCT/EP02/08724, filed Aug. 5, 2002, which in turn claims foreign priority to foreign application Germany 10139742.9, filed Aug. 13, 2001.

The present invention relates to a device for performing immuno assays ("biochip" or "lab on chip"), a method for its fabrication, and the use of such device for performing immuno assays, e.g. EIA and ELISA. Furthermore, the present invention relates to the use of photo lithographically patternable dry film photo resist based on a material with functional chemical groups for the immobilization of biomolecules.

In the life sciences and in medical diagnostics the detection of (bio)chemical reactions, i.e. the detection of biologically relevant molecules in a defined material to be analyzed, is of major importance. In this context the development of so called biochips is permanently propelled. Biochips typically are made from miniaturized hybrid functional elements comprising biological and technical components, especially biomolecules on a surface (outside surface and/or inside surface) used as specific (biomolecular) interaction partners. Frequently the structure of these functional elements comprise columns and rows, forming the so called "chip-arrays". Since thousands of biological or biochemical functional elements may be arranged on one chip, those chips are commonly fabricated using micro technologies. Biological and biochemical functional elements that can be used are in particular DNA, RNA, PNA, (using nucleic acids and their chemical derivatives e.g. single strands, triplex structures or combinations of those can be used), saccharides, peptides, proteines (e.g. antibodies, antigens, receptors), derivatives from combinatorial chemistry (e.g. organic molecules), cellular components (e.g. organelles), cells, multicellular organisms and cell assemblies.

Typically biochips comprise a 2D-base surface for the coating with biological oder biochemical functional materials. The base surfaces may e.g. also be formed by walls of one or more capillaries or channels, respectively. An extension of the geometry is a 3D-structure, where the analysis and also the manipulation or control respectively of reactions can be performed in a 2D-arrangement. Current state of the art technologies available for the fabrication of biochips typically require a chemical functionalization of the micro structure surfaces before the coupling or binding of the biological or biochemical functional elements. In particular, this can be achieved by activation of photosensitive groups in predefined locations of a substrate surface by means of localized light exposure of the substrate using an exposure matrix (see e.g. DE 199 40 752 A1). But the chemical functionalization of the micro structured surfaces required for the immobilization of the biomolecules aggravates production requirements for the fabrication of such biochips considerably, making such techniques not only little reliable but also very cost ineffective. Immobilization of the biomolecules using adsorption techniques also generates a huge effort for the surface coating.

Thus, the object of the present invention is to provide a simple, flexible, and cost effective method for the fabrication of so called "lab on chips" or "biochips", that especially eases the localized linking of biological or biochemical functional elements, namely it should avoid the problems associated with the chemical functionalization of the micro structure surface required for the localized linking of biological or biochemical functional elements.

This object is solved by the embodiments as characterized in the claims.

In particular, there is provided a method for the fabrication of a device for performing immuno assays, comprising:
(a) providing a micro structured substrate having predefined indentations and/or through holes,
(b) applying at least one layer of a dry film photo resist material with functional chemical groups onto said substrate,
(c) light exposing the dry film photo resist using a photo mask with a predefined pattern,
(d) developing the dry film photo resist layer,
(e) repeating step (b) and step (c) using a photo mask with a different predefined pattern and step (d), so that substrate and dry film photo resist material form a capillary structure or capillary channel structure, respectively, with at least one inlet and outlet,
(f) localized immobilizing biomolecules to at least one region of the inner surfaces of the dry film photo resist material channel structure generated in step
(e) by chemical coupling via the functional groups of the dry film photo resist material, wherein a device for performing immuno assays is obtained.

The present invention presents a novel technology platform for the cost effective, flexible, and reliable fabrication of devices, that is particularly useful for performing immuno assays (so called "lab on chips" or "biochips").

Figure 1:
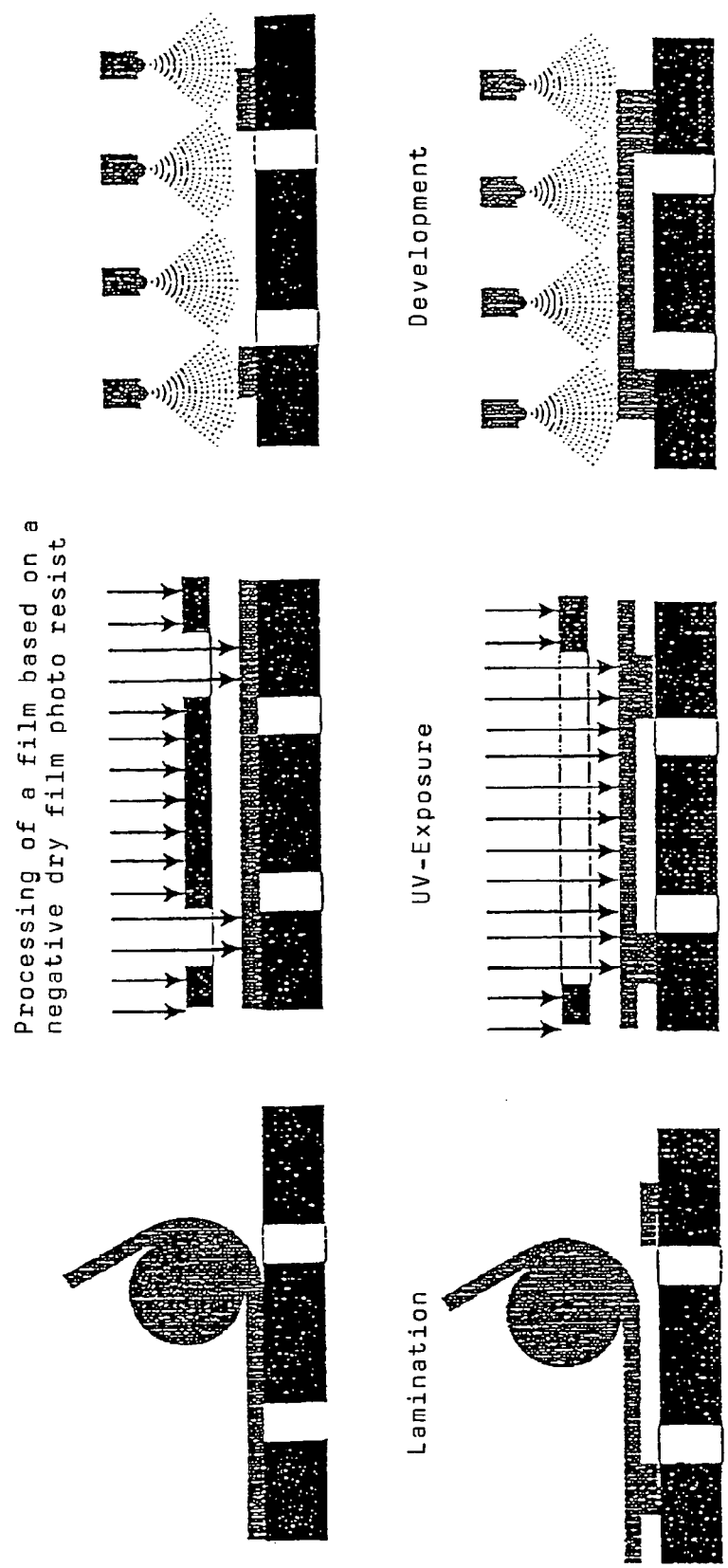
FIG. 1 is an example scheme showing the fabrication of a capillary channel system according to the present invention.

The dry film photo resist materials used in the method of the present invention are based on photo patternable polymers that comprise functional chemical groups which are able to form a chemical link with respective biomolecules. Preferably a dry film photo resist based on a negative photo resist is used in the method according to the present invention. In particular dry film photo resists based on polymeric materials comprising functional groups selected from carboxylic acids, carboxylic acids anhydrids, carboxylic acid chlorides, aldehydes, glyoxals, N-hydroxy succinimide esters, hydrazides, imidates, isothiocyanates, isocyanates, maleinimides, halogenquinones, epoxides, aziridines, acylazides, phenoles, amino groups, thiol groups, hydroxyl groups, sulfhydryl-reactive bromium and iodine, and biotin groups. Preferably, the chemical functional groups are thiol groups (—SH) and groups derived therefrom as e.g. pyridyl thio groups, carboxylic acid groups (—COOH) and groups derived therefrom such as e.g. carboxylic acid anhydride groups like maleic acid anhydride or succinic acid anhydride, imide ester groups such as e.g. N-hydroxy-succinimide ester groups, and carboxylate groups. Especially preferred are carboxylic acid groups. In a preferred embodiment of the present invention the dry film photo resist is based on a mixture of polymers and optionally oligomers and/or monomers, wherein at least one of the polymers, oligomers or monomers comprises thiol-, carboxylic acid-, anhydride-, acid-amide- or imide ester groups, preferable acrylic acid-, methacrylic acid-, maleic acid anhydride-, maleic acid imide- or N-hydroxy succinimide ester groups. The polymers used in such mixture may be block polymers, copolymers or graft copolymers, in particular copolymers, preferably random or block-copolymers which preferably comprise carboxylic acid-, anhydride-, acid amide- or imide ester groups. For example, photo resist materials on the basis of styrene/maleic acid anhydride-copolymers can be mentioned. Of course such mixture may comprise additional additives as e.g. fillers, cross linkers, plasticizers, and photo initiators, as well known to an expert in the field of dry film photo resists. In the course of the present invention, there is included the mixing or compounding of an aforementioned dry film photo resist material based on polymers with a monomer or oligomer, that on the one side is capable of being incorporated into the polymer network in the light induced cross linking reaction and on the other side comprises one of the aforementioned functional chemical groups which are capable to form a chemical link with respective biomolecules. Examples are γ-malein imido butyric acid-N-hydroxy succinimide, γ-malein imido capronic-acid-N-hydroxy succinimide oder N-acryloxy succinimide.

Dry Film Photo Resist Materials useful in the Present Invention are e.g. Vacrel® or Riston®, Both Manufactured by Dupont Since already the photo resist material that is used in combination with the substrate to fabricate the capillary structures by means of a photo lithographic process, is comprising functional chemical groups, the surface of the capillary channel system made from this dry film photo resist comprises, as the material itself, a high concentration of functional groups, in particular free carboxylic acid groups, enabling permanent chemical immobilization of biomolecules to this surface. Processing of the dry film resist material can be done especially advantageous using printed circuit board technologies to fabricate corresponding micro structures, namely channels and capillaries, respectively.

The substrate or carrier with predefined micro structured indentations and/or through holes can be a substrate for printed circuit boards or for semiconductors, a glass substrate or a polymer substrate, or also a non-patterned or already patterned dry film photo resist material. The predefined indentations and/or through holes can be made by e.g. using conventional photo lithographic processes and etching processes. In case of an already patterned dry film photo resist material this can be achieved in the preceding patterning process.

By repeated lamination and photo patterning using different photo masks, closed capillary structures or at least parts of channels or capillaries, respectively, comprising at least one inlet and one outlet, can be fabricated by the method according to the present invention. Typical dimensions of such channel structures produced in step (e) according to the method of the present invention are e.g. heights from 10 to 100 µm, widths of 10 to 500 µm and lengths of 10 to 1000 mm. The channels may be straight or meandering and continuous or comb-shaped arranged. Furthermore they can be arranged in one or two dimensional arrays, in one plane or stacked in multiple planes. Accordingly, the method according to the present invention also allows the fabrication of three dimensional arrays. If the capillary structure(s) is/are stacked in multiple planes, the capillaries may be connected by vertical channels. Zero dimensional (a single capillary), one dimensional or two dimensional arrays may be vertically stacked or can also be interconnected fluidically in such configuration by means of vertical openings.

In one embodiment of the method according to the present invention the functional chemical groups can be activated before step (f). If the dry film photo resist is based on polymers comprising carboxylic acid groups, this activation can be e.g. done by reaction with a carbodiimide compound such as dicyclohexylcarbodiimid (DCC). Such carbodiimide solution can be pumped through at least parts of the channel system, wherein the carboxylic acid groups are activated. Subsequently, the thus activated inner surfaces are coated at those sites of the channel system, which are formed by the dry film photo resist material, with the respectively selected biomolecules, such as e.g. an antibody, by chemical link with them.

In one embodiment of the method according to the present invention step (f) can be carried out by using immersion or pouring processes with subsequent sealing of the capillary structure with a top layer of at least one dry film photo resist. Alternatively, with exception of the channels provided as inlets and outlets, the capillary structure can be closed in the course of step (e) and subsequently step (f) can be carried out by using pumping processes. Furthermore in step (f) also a solution of biomolecules can be delivered to one or more capillaries of the capillary structure obtained in step (e) with at least one needle or needle arrangement utilizing capillary forces. For example, an excess of fluid can be delivered by a needle or an instrument comprising multiple needles to a vertical opening of such a capillary in a way that this capillary fills with this fluid by capillary forces. After the desired reaction time the fluid can be removed from the capillary by applying excess pressure. An also advantageous embodiment uses openings in the capillaries solely used for the immobilization of the biomolecules that is closed after the immobilization, e.g. with a dry film resist or a pressure sensitive adhesive.

Useful biomolecules for the localized and selective direct chemical coupling of step (f) to the functional groups of the dry film photo resist material to at least one region of the inner surface formed by the dry film photo resist material capillary structure made in step (e) are in particular DNA, RNA, PNA, (using nucleic acids and their chemical derivatives e.g. single strands, triplex structures or combinations of those can be used), saccharides, peptides, proteines (e.g. antibodies, antigens, receptors), derivatives from combinatorial chemistry (e.g. organic molecules), cellular components (e.g. organelles), cells, multicellular organisms and cell assemblies. If the device is intended to be used for performing EIA or ELISA, biomolecules used are in particular specific antibodies immobilized in step (f) localized and selective by chemical coupling to the functional groups of the dry film photo resist material to at least one region of the inner surface formed by the dry film photo resist material capillary structure obtained in step (e).

In a preferred embodiment of the present invention at least one capillary of the capillary structure is made as affinity capillary by immobilization of biomolecules and at least one capillary of the capillary structure is made as amplification capillary. The function of the amplification capillary is basically to amplify the chemical signal generated in the affinity capillary, by passing an analyte or sample solution, as e.g. a serum sample, by a cycling process. Preferably the channels of the amplification capillary are fabricated simultaneously with the affinity capillary, wherein affinity capillary and amplification capillary can be directly connected with each other. One amplification capillary can be provided for one affinity capillary. Multiple affinity capillaries can end into one amplification capillary, alternatively one affinity capillary can end in multiple amplification capillaries. Moreover, affinity- and amplification capillary can be arranged in one plane or fabricated separately and stacked vertically for use.

When passing a fluid to be analyzed (analyte) the chemical signal resulting from the interaction with the localized immobilized biomolecules is preferably measured electrochemically, preferably amperometrically, or spectrophotometrically or fluorescence spectrophotometrically.

If the chemical signal is e.g. generated glucose—if the biomolecule immobilized in step (f) localized and selective by direct chemical coupling to the functional groups of the dry film photo resist material to at least one region of the inner surface formed by the dry film photo resist material capillary structure obtained in step (e) is e.g. alkaline phosphatase and the analyte passed through the capillary structure contains glucose-6-phosphate—the resulting chemical signal, i.e. in the example glucose, can be converted multiple times, using one or more amplification capillaries, in a cyclic process according to the following scheme and accordingly amplified depending on the number of cycles:

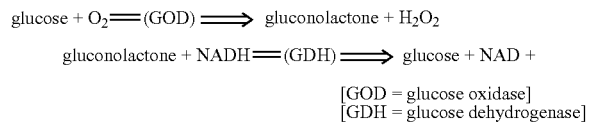

[GOD = glucose oxidase]
[GDH = glucose dehydrogenase]

In each cycle one molecule, i.e. in the example glucose, is formed. In the preceding exemplary reaction scheme hydrogen peroxide ($H_2O_2$) is formed that is oxidized on an electrode and quantified in this way.

The degree of the signal amplification induced by the amplification capillary basically depends on the velocity of the cyclic reactions (approx. the product of the respective enzymatic activities—in the preceding example GOD and GDH), the number of cycles and the glucose concentration.

Preferably, the amplification capillary is functionalized by immobilization of at least two enzymes that convert the chemical signal of the affinity capillary by a chemical cycling process into an amplified chemical signal. The immobilization of the enzymes to at least one region of the inner surface formed by the dry film photo resist material can either be done as the functionalization of the affinity capillary by chemical linking to the functional groups of the dry film photo resist material or by encapsulation into membranes or gels that cover one or more areas of the inner surfaces of the capillary. These membranes or gels can also advantageously be fabricated photo lithographically. The immobilization of the enzymes by gel entrapment allows for even higher volume activities. Of course such gel is occupying only a part of the channels cross section to allow a flow of analyte. Preferably the gel is bound by chemical links to at least one region of the inner surface of the channel system formed by the dry film photo resist material. This can be achieved by radical initiated cross linking of the gel in the capillary, wherein still remaining polymerizable groups of the dry film photo resist material participate in the radical reaction.

Figure 2:
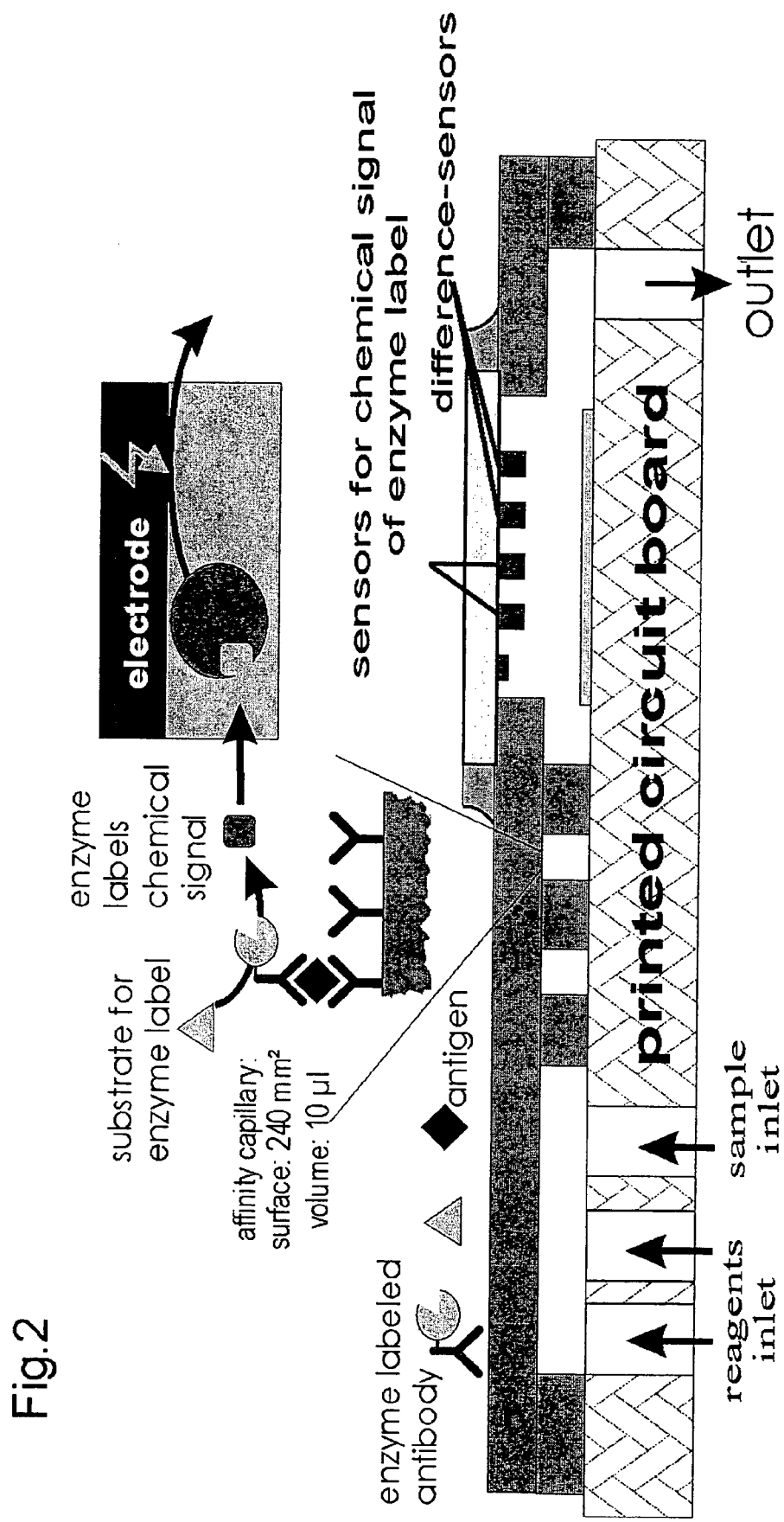
FIG. 2 is an example scheme showing the procedure for performing an ELISA using a capillary channel system according to the present invention.

Beside such "direct" analysis procedures, of course, also "indirect" immunological analysis of biologically active substances, such as EIA (enzyme-immunoassay) and ELISA (enzyme linked immunosorbent assay) can be performed according to the present invention, as exemplary shown in FIG. 2. For example the reaction between an antigen to be measured in a sample solution and a specific antibody, that is immobilized in step (f) localized and selective by chemical coupling to the functional groups of the dry film photo resist material to at least one region of the inner surfaces formed by the dry film photo resist material capillary structure produced in step (e), can be detected by a subsequent measurement of preferably an enzyme bound to the antigen (e.g. horseradish peroxidase or other plant, bacterial or animal enzymes). In general in an EIA the specificity of the antigen-antibody-reaction is coupled with an enzymatic reaction, by either using antibody- or antigen-enzyme-conjugates, that are measured via their enzymatic activity photometrically, fluorometrically or electrochemically after addition of a suitable substrate, wherein again an amplification capillary may be used for signal amplification. In the present invention, for ELISA the specific antibody against the antigen to be measured is immobilized in step (f) localized and selective by chemical coupling to the functional groups of the dry film photo resist material to at least one region of the inner surface formed by the dry film photo resist material capillary structure produced in step (e). To said antibody the antigen of the sample solution, e.g. a serum sample, binds and the remaining sample is washed off. Subsequently a second antibody coupled to a fully functional enzyme is added, binding to the already bound antigen. The enzyme-activity of the enzyme coupled via the antibody-antigen-antibodies conjugate to the capillary wall can be measured after addition of a suitable substrate, wherein also one or more amplification capillaries, as exemplified above, may be used.

A further subject matter of the present invention relates to a device for performing immuno assays comprising at least one substrate and provided thereon at least one dry film photo resist polymer material comprising functional chemical groups, wherein substrate and dry film photo resist polymer material form together a capillary structure with at least one inlet and one outlet, wherein biomolecules are chemically bound, via the functional groups of the dry film photo resist polymer material, to the inner surfaces of the capillary structure formed by the dry film photo resist material. The dry film photo resists, especially those based on negative photo resists, are based on the aforementioned photo patternable polymers, which comprise the aforementioned chemical groups. Especially, there are used dry film photo resists based on polymeric materials comprising functional groups selected from carboxylic acids, carboxylic acids anhydrids, carboxylic acid chlorides, aldehydes, glyoxals, N-hydroxy succinimide esters, hydrazides, imidates, isothiocyanates, isocyanates, maleinimides, halogenquinones, epoxides, aziridines, acylazides, phenoles, amino groups, thiol groups, hydroxyl groups, sulfhydryl-reactive bromium and iodine and biotin groups. Preferably, the chemical functional groups are thiol groups (—SH) and groups derived from them such as e.g. pyridyl thio groups, carboxylic acid groups (—COOH) and groups derived from them such as e.g. carboxylic acid anhydride groups like maleic acid anhydride or succinic acid anhydride, imide ester groups as e.g. N-hydroxy-succinimide ester groups, and carboxylate groups.

In a preferred embodiment of the present invention the dry film photo resist is based on a mixture of polymers and optionally oligomers and/or monomers and additional additives such as e.g. fillers, cross linkers, plasticizers, and photo initiators, wherein at least one of the polymers, oligomers or monomers comprises thiol-, carboxylic acid-, anhydride-, acid-amide- or imide ester groups, preferable acrylic acid-, methacrylic acid-, maleic acid anhydride-, maleic acid imide- or N-hydroxy succinimide ester groups. The polymers used in such mixture may be block polymers, copolymers oder graft copolymers, in particular copolymers, preferably random or block copolymers which preferably comprise carboxylic acid-, anhydride-, acid amide- or imide ester groups. In the present invention, there is also included the mixing or compounding of an aforementioned dry film photo resist material with a monomer or oligomer, that is on the one side capable of being incorporated into the polymer network in the light induced cross linking reaction and on the other side comprises one of the aforementioned functional chemical groups which are capable to form a chemical link with respective biomolecules. Examples are γ-malein imido butyric acid-N-hydroxy succinimide, γ-malein imido capronic-acid-N-hydroxy succinimide oder N-acryloxy succinimide.

Dry Film Photo Resist Materials useful in the Present Invention are e.g. Vacrel® Oder Riston®, Both Manufactured by Dupont The substrate or carrier with predefined micro structured indentations and/or through holes can be a substrate for printed circuit boards or for semiconductors, a glass substrate or a polymer substrate, or also a non-patterned or already patterned dry film photo resist material. As biomolecules DNA, RNA, PNA, (using nucleic acids and their chemical derivatives e.g. single strands, triplex structures or combinations of those can be used), saccharides, peptides, proteines (e.g. antibodies, antigens, receptors), derivatives from combinatorial chemistry (e.g. organic molecules), cellular components (e.g. organelles), cells, multicellular organisms and cell assemblies, can particularly be mentioned. If the device is intended to be used for performing EIA or ELISA, biomolecules used are in particular specific antibodies immobilized in step (f) localized and selective by chemical coupling to the functional groups of the dry film photo resist material to at least one region of the inner surface formed by the dry film photo resist material capillary structure made in step (e). In the device of the present invention preferably at least one capillary of the capillary structure is made as affinity capillary by immobilization of biomolecules and at least one capillary of the capillary structure is made as amplification capillary. The amplification capillary can e.g. be functionalized by at least two enzymes.

In a preferred embodiment of the present invention the device comprises at least two electrodes that can be provided for one capillary or multiple capillaries simultaneously. The electrodes can be made as micro electrodes or micro electrode arrays. In this embodiment the arrangement of the electrodes enables the electrochemical detection for the quantification of the chemical signal from the affinity or amplification capillary, respectively. At least two electrodes are in contact with the fluid to be analyzed. The electrodes, either one or all of them, can be fabricated or arranged, respectively, in the course of the fabrication of the channel system on the same carrier or substrate. Alternatively the electrodes, either one or all of them, can be fabricated separately from the capillaries and assembled in the course of the fabrication of the device or when the device is to be used. Either one such detection unit comprising at least two electrodes can be used for one capillary or alternatively it is used for multiple capillaries. Especially advantageous is amperometric measurement, where the chemical signal that e.g. is correlated to the concentration of the produced chemical species, is electrochemically converted at one or more electrodes which are polarized to a constant potential versus the solution resulting in a measurable current proportional to the concentration of said chemical species. Advantageously the electrodes are made as micro electrodes, e.g. also enzyme electrodes, or micro electrode arrays. Furthermore the chemical signal from the affinity or amplification capillary, respectively, can not only be directly converted at one or more of these electrodes, but can also, by means of enzymes entrapped in membranes on top of this electrode, become subjected to a chemical amplification. Moreover, one or more additional electrodes, where the described detection processes do not take place and whose signal is used to obtain a difference signal with the detecting electrode(s), by what the signal to noise ratio can be increased, can be implemented.

Alternatively also optical, namely spectrophotometric detection methods can be provided, especially such using fluorescence measurement. For this approach at least one part or the channel structure comprises an optical transparent lid.

For the use of the device according to the present invention initially the fluid to be analyzed is brought into the capillary system, namely into the at least one affinity capillary. The flow can either be interrupted for a certain time, to allow the affinity reaction, as e.g. antibody-antigen, to take place, or the flow is maintained for a certain time to increase the sensitivity by providing the transport of a larger amount of the substance to be detected or analyzed, respectively. After a washing step the affinity capillary is loaded with a solution of a detection-biomolecule (protein, antibody, DNA, RNA), which comprises catalytic activity e.g. by coupling with an enzyme (e.g. glucose oxidase, horseradish peroxidase or other bacterial, plant or animal enzymes). After the desired incubation time has elapsed, usually washing is carried out once again and the affinity capillary is loaded with a solution comprising a substance that is converted as a result of the catalytic activity of the bound biomolecule. Quantification of the assay can then be performed either by passing this solution continuously through the affinity capillary and eventually through the amplification capillary and through the detection unit or alternatively keeping the solution for the desired time in the affinity and/or the amplification capillary, resulting in a continuous accumulation of the species to be detected, wherein the fluid volume of the affinity capillary may be transferred to the amplification capillary, where the solution also remains for the desired time and finally this fluid volume is pumped into the detection unit comprising electrochemical and/or photometric measurement units.

The device or carrier, respectively, for the procedure for the measurement of an analyte according to the present invention is suitable for performing immuno assays, especially for the immunological determination of biologically active substances in body fluids. For example the reaction between an antibody that is directly bound through a chemical link to the functional groups of the dry film photo resist material to the inner surfaces of the capillary structure formed by the dry film photo resist material, and an antigen as a substance to be measured can be detected e.g. by the subsequent determination of an enzyme bound to said antigen or bound to the antibody. Such tests are useful for the measurement of drugs, hormones, and proteins.

A further subject matter of the present invention relates to the use of a photo lithographically patternable dry film photo resist based on a material comprising functional chemical groups for the immobilization of biomolecules. Preferably a dry film photo resist based on a negative photo resist is used. Especially dry film photo resists based on polymeric materials are employed, which contain functional groups selected from carboxylic acids, carboxylic acids anhydrids, carboxylic acid chlorides, aldehydes, glyoxals, N-hydroxy succinimide esters, hydrazides, imidates, isothiocyanates, isocyanates, maleinimides, halogenquinones, epoxides, aziridines, acylazides, phenoles, amino groups, thiol groups, hydroxyl groups, sulfhydryl-reactive bromium and iodine and biotin groups. Preferably the chemical functional groups are thiol groups (—SH) and groups derived from them such as e.g. pyridyl thio groups, carboxylic acid groups (—COOH) and groups derived from them such as e.g. carboxylic acid anhydride groups like maleic acid anhydride or succinic acid anhydride, imide ester groups such as e.g. N-hydroxy-succinimide ester groups, and carboxylate groups. Especially preferred are carboxylic acid groups. In a preferred embodiment of the present invention the dry film photo resist is based on a mixture of polymers and optionally oligomers and/or monomers and additional additives, as e.g. fillers, cross linkers, plasticizers, and photo initiators, wherein at least one of the polymers, oligomers or monomers comprises thiol-, carboxylic acid-, anhydride-, acid-amide- or imide ester groups, preferable acrylic acid-, methacrylic acid-, maleic acid anhydride-, maleic acid imide- or N-hydroxy succinimide ester groups. The polymers used in such mixture may be block polymers, copolymers or graft copolymers, in particular copolymers, preferably random or block copolymers, preferably comprising carboxylic acid-, anhydride-, acid amide- or imide ester groups. In the present invention, there is also included the mixing or compounding of an aforementioned dry film photo resist material based on polymers with a monomer or oligomer that is on the one side capable of being incorporated in the polymer network in the light induced cross linking reaction and on the other side comprises one of the aforementioned functional chemical groups which are capable to form a chemical link with respective biomolecules. Examples are γ-malein imido butyric acid-N-hydroxy succinimide, γ-malein imido capronic-acid-N-hydroxy succinimide oder N-acryloxy succinimide.

The invention claimed is:

1. A method for the fabrication of a device for performing immunoassays comprising:
   (a) providing a micro structured substrate having predefined indentations and/or through holes;
   (b) applying at least one layer of a dry film photo resist material, wherein the dry film photo resist comprises an outer surface facing away from the substrate and an inner surface facing toward the substrate, wherein the outer surface is subject to photo lithographic light and the inner surface comprises functional chemical groups attached thereto;
   (c) light exposing the dry film photo resist using a photo mask with a different predefined pattern;
   (d) developing the dry film photo resist layer;
   (e) repeating step (b) and step (c) using a photo mask with a different predefined pattern and step (d), so that substrate and dry film photo resist material form a capillary structure or capillary channel structure, respectively, with at least one inlet and outlet; and
   (f) localized immobilizing biomolecules to at least one region of the inner surface of the dry film photo resist material channel structure generated in step (e) by chemical coupling via the functional groups of the dry film photo resist material, wherein a device for performing immuno assays is obtained.

2. The method according to claim 1, wherein the dry film photo resist is based on a negative photo resist.

3. The method according to claim 1 or 2, wherein the functional chemical groups are selected from carboxylic acids, carboxylic acids anhydrids, carboxylic acid chlorides, aldehydes, glyoxals, N-hydroxy succinimide esters, hydrazides, imidates, isothiocyanates, isocyanates, maleinimides, halogenquinones, epoxides, aziridines, acylazides, phenoles, amino groups, thiol groups, hydroxyl groups, sulfhydryl-reactive bromium and iodine and biotin groups, preferably thiol groups (—SH) and groups derived therefrom and carboxylic acid groups (—COOH) and groups derived therefrom.

4. The method according to claim 1, wherein the dry film photo resist is based on a mixture of polymers and optionally oligomers and/or monomers, wherein at least one of the polymers, oligomers or monomers comprises thiol-, carboxylic acid-, anhydride-, acid-amide- or imide ester groups, preferably acrylic acid-, methacrylic acid-, maleic acid anhydride-, maleic acid imide- or N-hydroxy succinimide ester groups.

5. The method according claim 1, wherein the functional chemical groups are carboxylic acid groups, which are activated before step (f).

6. The method according to claim 3, wherein the activation, if the functional groups are carboxylic acid groups, and wherein activation of said carboxylic acid groups is carried out by reaction with a carbodiimide compound.

7. The method according to claim 1, wherein step (f) is performed by using an immersion or pouring process and the channels of the capillary structure are subsequently closed with either a top layer of at least one dry film photo resist layer or with a self sealing film.

8. The method according to claim 1, wherein in the course of step (e) the predefined channels of the capillary structure are closed, with the exception of the channels provided as inlets and outlets, and subsequently step (f) is performed by using pumping techniques.

9. The method according to claim 1, wherein in step (f) a solution of biomolecules is delivered to one or more capillaries of the capillary structure obtained in step (e) by means of at least one needle or an arrangement of needles utilizing capillary forces.

10. The method according to claim 1, wherein the biomolecules used in step (f) are DNA, RNA, PNA, saccharides, peptides, proteines, cellular components, cells, multicellular organisms and cell assemblies.

11. The method according to claim 1, wherein by binding of biomolecules, at least one capillary of the capillary structure is made as affinity capillary and at least one capillary is made as amplification capillary.

12. The method according to claim 11, wherein the amplification capillary is functionalized by immobilization of at least two enzymes.

13. The method according to claim 12, wherein the immobilization of the enzymes to at least one region of the inner surface of the capillary structure formed by the dry film photo resist material, is carried out by chemical linking via the functional groups of the dry film photo resist material or by entrapment into a membrane that covers one or more of the inner surfaces of the capillary structure.

14. The method according to claim 13, wherein the membrane is fabricated photo lithographically.

15. The method according to claim 1, wherein the chemical signal, generated due to the interaction of the bound biomolecules with a passing fluid to be analyzed, is measured electrochemically, preferably amperometrically, or fluorescence spectrophotometrically.

* * * * *